United States Patent [19]

Dattilo

[11] Patent Number: 4,677,426
[45] Date of Patent: Jun. 30, 1987

[54] DUST DETECTING RING ASSEMBLY

[75] Inventor: Donald P. Dattilo, Louisville, Ky.

[73] Assignee: Electronic Dust Detection, Inc., Louisville, Ky.

[21] Appl. No.: 854,713

[22] Filed: Apr. 16, 1986

Related U.S. Application Data

[63] Continuation of Ser. No. 461,689, Jan. 28, 1983, abandoned.

[51] Int. Cl.$^4$ ............................................. G08B 21/00
[52] U.S. Cl. ................................. 340/627; 250/222.2; 324/71.4; 340/664; 340/687; 356/439
[58] Field of Search ............... 340/627, 630, 687, 664; 356/338, 432, 437–439; 250/564–565, 573–574, 221, 222.1, 222.2; 362/366–367, 230, 234, 252; 377/53; 324/71.4

[56] References Cited

U.S. PATENT DOCUMENTS

| | | | |
|---|---|---|---|
| 2,571,974 | 10/1951 | Walker | 250/222.2 X |
| 3,652,850 | 3/1972 | Briggs | 250/222.2 X |
| 3,727,056 | 4/1973 | Enemark | 356/439 X |
| 3,820,897 | 6/1974 | Roess | 356/438 X |
| 3,845,480 | 10/1974 | Steinberg | 340/627 |
| 3,994,603 | 11/1976 | Paschedag | 340/630 X |
| 4,001,800 | 1/1977 | Franks | 340/630 |
| 4,005,311 | 1/1977 | Ledley | 250/221 X |
| 4,017,193 | 4/1977 | Loiterman | 356/438 X |
| 4,051,763 | 10/1977 | Thomanek | 250/222.2 X |
| 4,080,076 | 3/1978 | Carr | 250/565 X |
| 4,121,201 | 10/1978 | Weathers | 340/687 X |
| 4,155,653 | 5/1979 | San Miguel et al. | 340/630 X |
| 4,201,471 | 5/1980 | Pitt et al. | 356/338 X |
| 4,245,910 | 1/1981 | Källander | 340/627 X |
| 4,356,387 | 10/1982 | Tsubota et al. | 377/53 X |
| 4,459,476 | 7/1984 | Weissmueller et al. | 250/221 |
| 4,479,053 | 10/1984 | Johnston | 250/221 |
| 4,506,161 | 3/1985 | Muggli et al. | 340/630 X |

FOREIGN PATENT DOCUMENTS

| | | | |
|---|---|---|---|
| 8204150 | 11/1982 | Sweden | 250/574 |
| 0853499 | 8/1981 | U.S.S.R. | 250/564 |

OTHER PUBLICATIONS

Gucker, Jr., et al., "A Photoelectric Counter for Colloidal Particles", American Chemical Society, vol. 69, pp. 2422–2431, Mar. 1937.

Primary Examiner—Glen R. Swann, III
Assistant Examiner—Thomas J. Mullen, Jr.
Attorney, Agent, or Firm—Cox & Smith Incorporated

[57] ABSTRACT

A dust detector ring assembly for detecting extremely small quantities of particulate contamination in air being taken into the carburetor of an engine is disclosed. The assembly includes a series of infrared light emitting diodes alternately interposed with a like series of infrared light detecting diodes and arranged in a circle around an interior surface portion of a frame defining a passageway of circular cross-section therethrough. A light beam generated by each of the emitters is directed against a different one of the detectors so that the light beams intersect one another at a common point in the passageway. The sensitivity of the assembly is thus greatest at the common point of intersection of the light beams and decreases proportionally moving away from the intersection point toward the defining surface of the passageway. A flexible circuit board is formed in a circle and is connected to the emitters and detectors. A flat circuit board is connected to the circular circuit board. The emitters and detectors are inserted into shafts radially projecting through an annular retaining ring. A ring-shaped infrared light glass filter is attached to an interior surface of the retaining ring and defines the passageway. An electronic circuit for sensing and counting interruptions of the light beams and for activating an alarm when potentially engine-damaging amounts of particulate matter flow into an engine carburetor air intake system is also disclosed.

20 Claims, 8 Drawing Figures

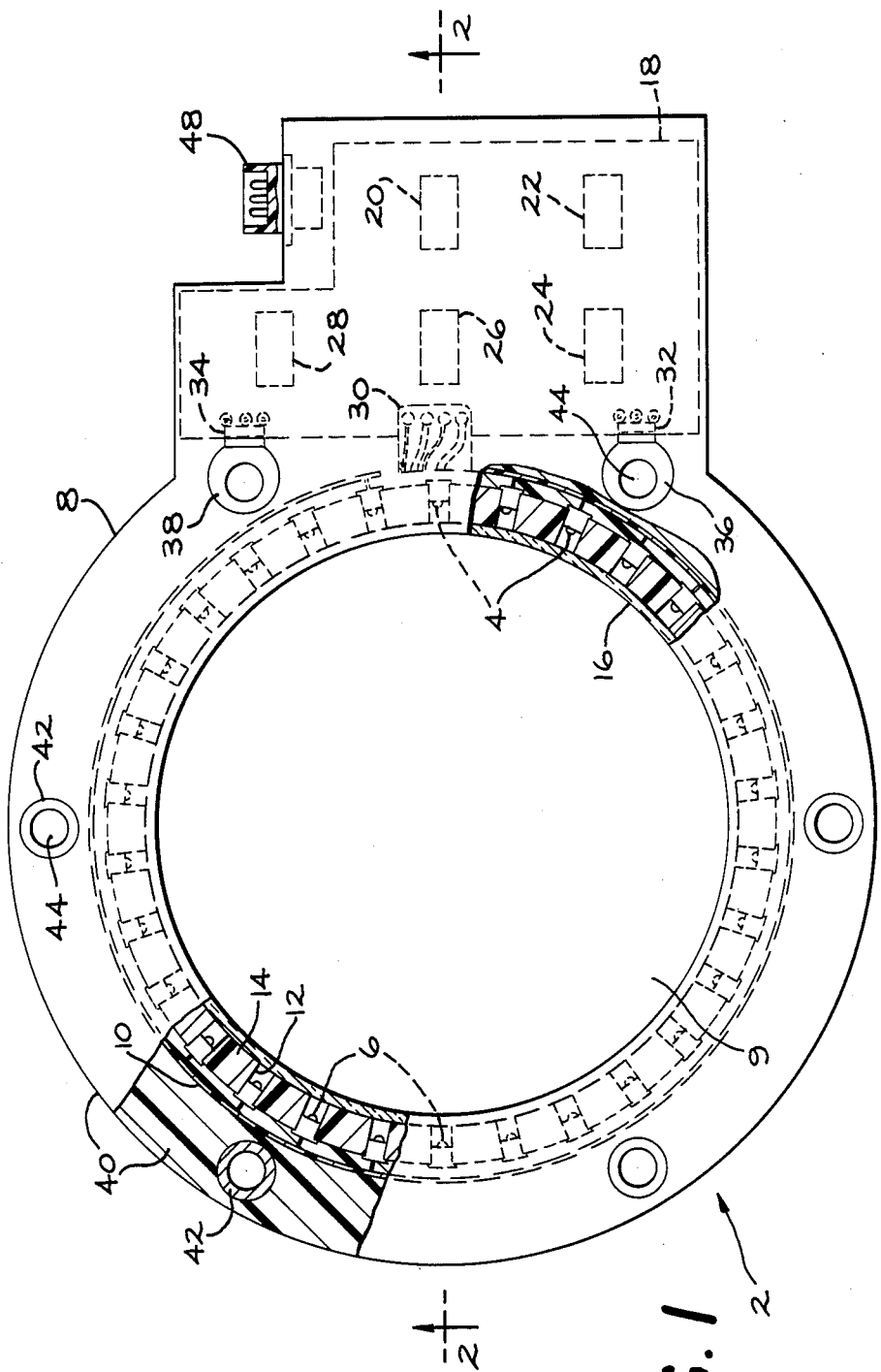
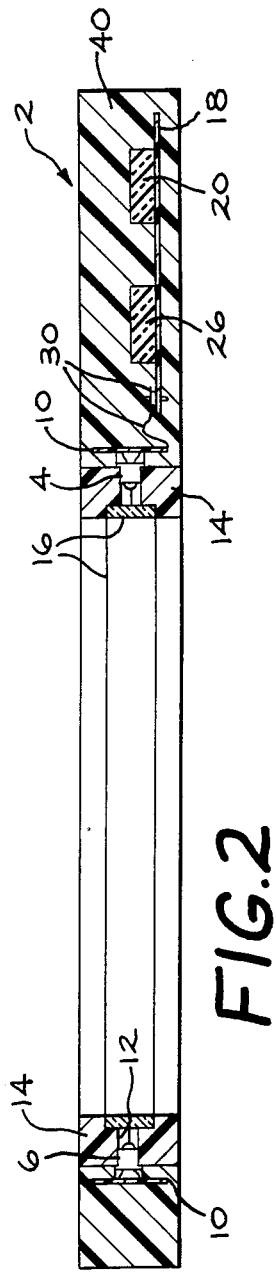
FIG.1
FIG.2

DUST DETECTING RING ASSEMBLY

This application is a continuation of application Ser. No. 461,689, filed Jan. 28, 1983 now abandoned.

BACKGROUND OF THE INVENTION

This invention relates to photodetector devices for detecting the presence of particulate matter in a gaseous medium such as air.

Such devices, generally speaking, have long been known and used in the prior art. See, for example, the smoke measuring transducer disclosed in U.S. Pat. No. 4,155,653 issued to A. San Miguel, et al. on May 22, 1979 and the particle detector disclosed in U.S. Pat. No. 4,245,910 issued to S. Kallander on Jan. 20, 1981. The first mentioned prior art device utilizes photoelectric detection by means of a single light beam passing between an emitter and a detector across a chamber containing air such tnat the amount of smoke or particulate matter in the air can be measured by determining the opacity or transmissivity thereof. The second prior art device also employs a single light emitter and detector wherein the emitter is disposed at one of two focal points in an elliptical reflecting chamber. The collector is placed at the other focal point so that light from the emitter is not only beamed directly against the collector but is also reflected off of the surrounding elliptically-shaped chamber surface against the collector. Numerous other arrangements of single beam photodetector systems for use in dust detection are also known in the prior art.

These prior art detectors thus sense the average opacity of a gas, such as air, contained in a detection chamber to provide a measure of the average amount of particulate matter contained in the gas. Such detectors are not adapted to sense the presence of individual dust particles in the gas which may be traveling at high speeds, as, for example, in a carburetor air intake system. Neither are such devices adapted to react extremely quickly to such individual particles so as to rapidly alert an engine operator to the presence of a small quantity of potentially engine damaging particles. These devices are adapted to measure the presence of particulate matter in a gas by sensing the attenuation of a light beam directed across a gas filled chamber rather than by sensing the interruption of the beam caused by particles flowing through the chamber at high speeds.

By means of my invention, these and other difficulties encountered in the prior art are substantially reduced or eliminated.

SUMMARY OF THE INVENTION

It is an object of the present invention to provide a highly sensitive assembly for use in detecting the presence of particulate matter contained in a gaseous medium flowing at a high rate of speed.

It is another object of the present invention to provide a dust detector assembly for use in a gaseous medium which has rapid acting capability of alerting an operator to the presence of dust in the medium.

It is also an object of the present invention to provide a compact dust detector assembly of rugged construction suitable for use in a carburetor air intake line of an engine.

Briefly, in accordance with the present invention, there is provided an assembly for use in detecting the presence of particulate matter in a gaseous medium which includes frame means defining a passageway therethrough. A plurality of light sources is mounted in the frame and arranged to direct as many light beams across said passageway to form a light beam grid. A like plurality of photodetector means is mounted in the frame, each of which is arranged in receiving relation to a light beam from a different one of the light sources. Lastly, circuit means is mounted in the frame for electrically energizing the sources and photodetector means and for generating an output signal indicative of interruption of any one or more of said light beams.

These and other objects, features and advantages of the present invention will become apparent to those skilled in the art from the following detailed description and attached drawings upon which, by way of example, only a preferred embodiment of the invention is illustrated.

BRIEF DESCRIPTION OF THE DRAWINGS

FIG. 1 shows an end view of a dust detector ring assembly, thus illustrating one preferred embodiment of the subject invention.

FIG. 2 shows a cross-sectional side view of the detector ring assembly of FIG. 1 as viewed along cross-section lines 2—2 of the latter figure.

DESCRIPTION OF THE PREFERRED EMBODIMENT

Figure 3:
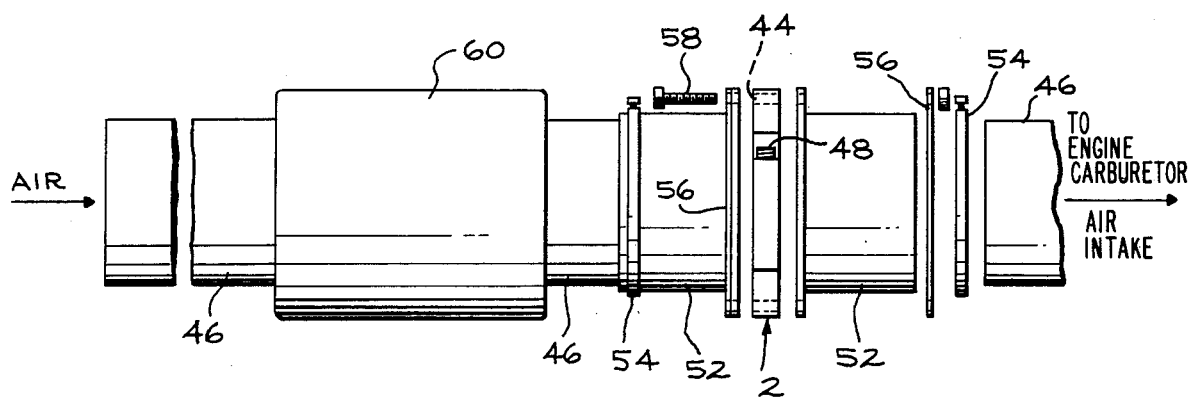
FIG. 3 shows an exploded side elevation view of a portion of a carburetor air intake system for a conventional engine illustrating connection of the assembly of FIG. 1 therein.

Referring now to the drawing figures, there is shown, in one preferred embodiment of the invention, a dust detector ring assembly 2 having a series of infrared light emitting diodes or emitters 4 alternately interposed with a like series of infrared light detecting diodes or detectors 6, both of which are arranged in a circle around an interior surface portion of a ring-shaped frame 8. Each of the emitters 4 is arranged so as to direct a light beam through a passageway or hollow central portion 9 of the frame 8 upon a different one of the detectors 6 which is diametrically opposite thereto. The emitters 4 and detectors 6 are connected in standoff fashion to a conventional flexible circuit board 10 which is bent upon itself into the form of a circular ring with the emitters 4 and detectors 6 being inserted into hollow shafts 12 formed through a plastic retaining ring 14. A glass infrared light filter 16 is glued or otherwise attached to the retaining ring 14 to form the interior surface of the frame 8 and defines the hollow circular central portion 9. The filter 16 is opaque with respect to all wavelengths of visible light and transparent with respect to infrared light. A flat circuit board 18 containing a series of integrated microcircuits or ICS 20, 22, 24, 26 and 28 is electrically connected to the circuit board 10 by means of a terminal strip 30. The board 18 also contains a pair of ICs 32 and 34 connected respectively to a pair of hollow cylindrically-shaped supporting members 36 and 38, which also function as heat sinks, together with numerous other discrete components as shown in FIGS. 5-8. The aforementioned components and structural elements are encased in a suitable epoxy 40 to seal and rigidify the assembly 2 as shown in FIGS. 1-3. A series of hollow steel cylindrical elements 42 disposed through the epoxy 40 are annularly spaced around a portion of the frame 8 and, together with the two hollow heat sink members 36 and 38, form bolt holes 44 for installing the assembly 2 in an engine carburetor air intake line 46 as shown, for example, in FIG. 3. A suitable multi-pin electrical connector 48 connects the circuitry of the circuit board 18 by means of a suitable cable, not shown, to an alarm circuit 49, a conventional electromechanical counter circuit 50 and a regulator circuit 51 (See FIGS. 5-7), all of which are remotely located with respect to the assembly 2 as, for example, in a truck cab, not shown.

Referring now specifically to FIG. 3, the assembly 2 may be placed in the carburetor air line 46 between two hollow rubber sleeves 52 which are, in turn, clamped upon the ends of the pipes forming the line 46 by means of conventional ring clamps 54. Metal rings 56 which form spacers or washers are slipped over the body of the sleeves 52 against the flanged ends thereof, whereby the assembly 2, sleeves 52 and rings 56 are securely fastened together by means of bolts 58. The assembly 2 may be used to monitor the amount of dust or particulate matter flowing to the engine carburetor from the intake end of the line 46 through a conventional air filter 60. In such cases, the assembly 2, should be disposed between the engine carburetor and the air filter 60 as shown in FIG. 3. Upon breakdown of the air filter 60 or for any other reason that would cause potentially engine-damaging particulate matter to flow past the filter 60 to the carburetor, the assembly 2 will be in position to monitor the event and actuate an alarm horn 62 (See FIG. 6) to notify the engine operator of the problem.

In the present example of the invention, the assembly 2 contains thirty emitters 4 and detectors 6 alternately interposed with one another and annularly spaced apart every 12 degrees around the circular portion of the frame 8. The diameter of the central portion 9 in this particular arrangement is six inches but should in each case be approximately equal to the inside diameter of the air intake line 46 in which it is to be used. A greater or lesser number of emitters 4 and detectors 6 may be arranged in a circle around the frame 8 as desired depending, at least in part, upon the diameter of the central portion 9 and the sensitivity of the assembly 2 that may be required for a given application.

Assuming that the air line 46 is essentially straight for sufficient distances on both sides of the assembly 2, a volume of air 64, together with any quantity of particulate matter that may be contained therein, flowing through the frame 8 will be most heavily concentrated near the axial center of the central portion 9 and will decrease proportionately across the space to the surface of the filter 16. Similarly, due to the circular arrangement of the emitters 4 and detectors 6 around the frame 8, the sensitivity of the assembly 2 to particulate matter flowing therethrough will be greatest at the axial center of the central portion 9 and will decrease proportionately across the space to the surface of the filter 16.

Referring now to the electronic circuitry associated with the assembly 2, the detectors 6 are conventional high speed PIN type photodiodes which are responsive to optical energy in the infrared portion of the electromagnetic spectrum. Each of the detectors 6, numbering fifteen in the present example, are series-connected to a separate 10 MegOhm resistor 21 to limit the current flow through each detector to the nanoampere range. The relatively high impedance of each of the resulting resistor/detector combinations, connected as they are in reverse bias fashion, results in high sensitivity and high speed response to particulate matter flowing through the frame 8 and produces a detector circuit with excellent signal-to-noise ratio. Each of the subject resistor/detector combinations is connected in parallel through a different high speed switching diode 23, a total of fifteen of which are also used in the present example, to form an OR logic circuit. Accordingly, conduction of any one of the resistor/detector combinations has no significant effect on the sensitivity of the remaining combinations. The resulting OR circuit presents a high impedance on an input line 65 and to a non-inverting input terminal of a current differentiating Norton operational amplifier or comparator 20a. When particulate matter flowing through the central portion 9 breaks one or more of the infrared light beams between the emitters 4 and detectors 6, current flow in the comparator input line 65 exceeds a certain threshold current level in a comparator reference line 66 connected to an inverting input terminal of the comparator 20a and produces a signal on a comparator output line 68. The desired reference input current is established by a voltage divider network 70. The current level established in the line 66 by the network 70 represents the desired particle density above which the comparator 20a will be triggered. The line 68 is connected to a Schmidt trigger 20b which is adapted to generate a 500 kHz output signal on a line 71 whenever a signal exists on the line 68. The output line 68 is connected through a resistor 67 to an inverting input terminal of the Schmitt trigger 20b to present a high impedance at that terminal. An output line 71 is connected back to a non-inverting input terminal of the Schmitt trigger 20b to increase its switching speed in response to an input signal on the line 68. The output line 71 is also connected back to the non-inverting input line 65 of the comparator 20a to cause the circuit of comparator 20a and Schmitt trigger 20b to oscillate whenever a signal on the line 65 exceeds the reference signal on the line 66. A trigger input terminal of a one-pulse or one-shot generator 22a is connected to the line 71, an output line 72 of which goes high for a suitable time, for example 22 milliseconds, upon receipt of the first 500 kHz pulse from the line 71. If, at the end of this 22 ms. time period, the pulses on the line 71 have ceased, the generator 22a will become inactive and the line 72 will go low until another 500 kHz pulse is received. If, on the other hand, 500 kHz pulses are still present on the line 71 at the end of this 22 ms. period, the generator 22a will rapidly reset itself and maintain the output pulse on the line 72 for an additional 22 ms. duration. The generator 22a will continue to rapidly reset itself and maintain high output levels on the line 72 for successive 22 ms. durations so long as 500 kHz input pulses are present on the line 71 at the end of each succeeding 22 ms. time period. The line 72 is operatively connected to a 72 Hz oscillator 22b so that when a 22 ms. pulse is received, a 13.8 ms. pulse is generated on a line 74. The line 74 is connected by a line 76 through a pair of inverters 24a,b (FIG. 5 only) to the counter circuit 50, whereby a conventional electromechanical counter 80 registers or updates by one unit for each 13.8 ms. pulse received.

The line 74 is also connected to a line 82 to present the 13.8 ms. pulses to the IC 26 which is connected as a decade counter to count from 0 to 9 as 10 successive pulses are received on the line 82, then reset itself to 0, and repeat the count so long as a steady stream of input pulses occurs. If the pulses on the line 82 are interruped, the counter 26 resets itself to 0 at that time regardless of the size of the count at the time of the interruption. When the counter 26 reaches a count of 8, meaning that it has received 9 successive 13.8 ms. pulses without interruption, a counter output line 84 goes high to drive IC 28a which forms an alarm latch circuit. The circuit 28a, in turn, activates a remotely located alarm power driver circuit 86 through a line 87 to operate the horn 62 and an alarm lamp driver IC 88 to energize a display lamp 90. Those skilled in the art will appreciate that the circuit 86 can also be used to activate a solenoid or other conventional device to shut down the engine at the same time the alarm horn 62 is activated if desired. A horn load check circuit 92 is connected between a 12.5 volt d.c. source and ground through the horn 62 such that an alarm load check lamp 94 glows at all times when the circuit is energized and when the horn 62 is properly connected so as to be operational. If the horn 62 is disconnected for any reason, the lamp 94 goes out to indicate the fault. In the circuit of the present example, the horn 62 will be activated when the detectors 6 have sensed beam breaking particle flow through the frame 8 continuously for a period of 194 milliseconds. Those skilled in the art will appreciate that this time lapse can be readily increased or decreased as needed. Once the horn 62 is activated, it will remain active until the alarm latch circuit 28a is reset by removing source potential from across the lines 63a,b (See FIG. 7). The lines 63a,b are connected to a remotely located conventional main d.c. power source of from 12 to 36 volts.

An IC 96 is connected as a cable check circuit and lamp driver to drive a cable fault lamp 98 to indicate when the cable from the connector 48 to the display circuitry is disconnected, loose or otherwise faulty. The lamp 98 blinks due to oscillation of the IC 96 when a cable ground 99 is broken (See FIGS. 6 and 8). The IC 96 is connected through a line 99 and the cable to the regulated 5.0 volt d.c. power supply 100. A power-on check circuit containing a power-on lamp 101 is connected to the 12.5 v.d.c. supply line of the circuit 51 (FIG. 7) and is adapted to glow so long as electrical power is thus supplied.

Figure 4:
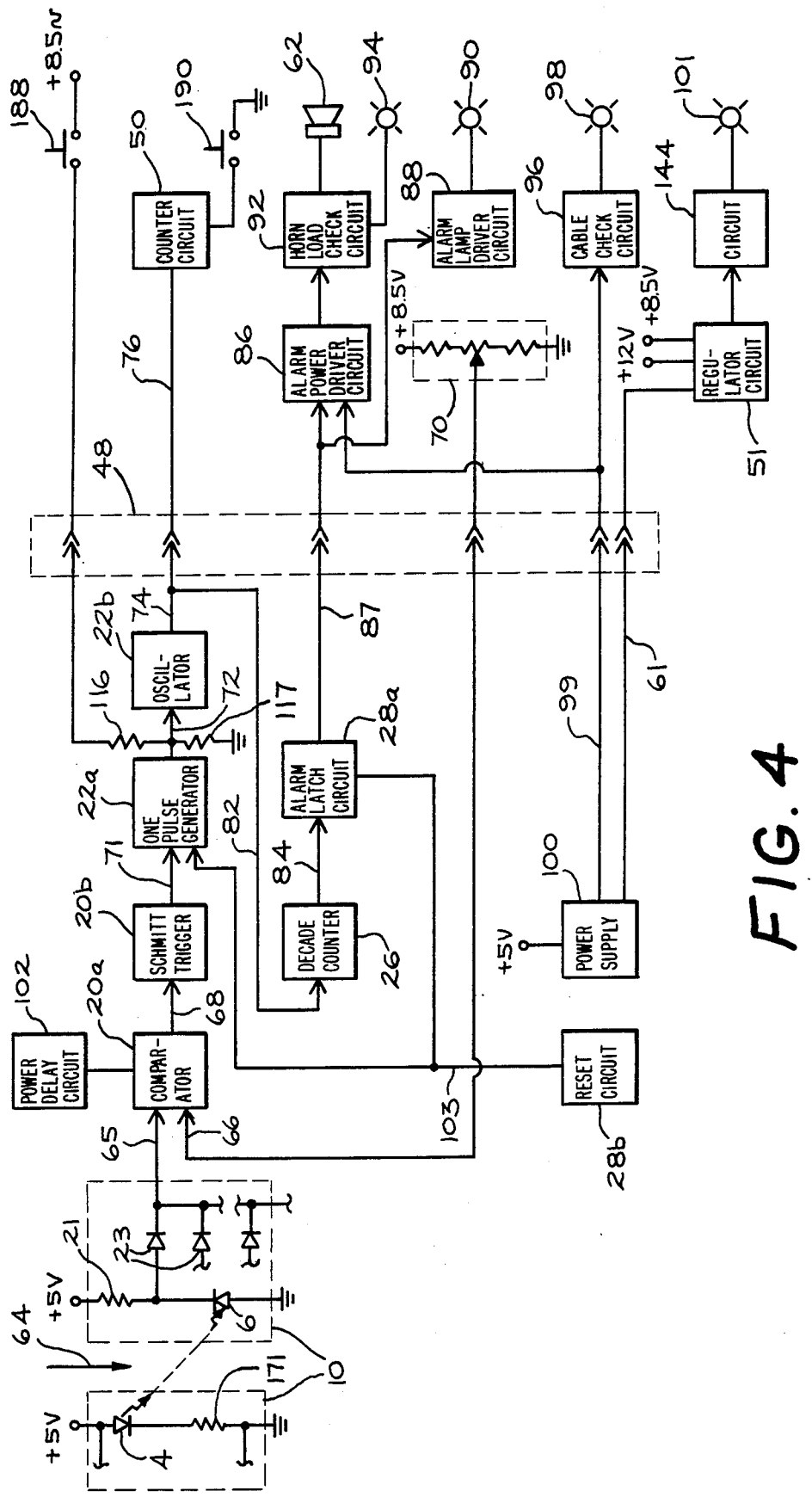
FIG. 4 shows a functional block diagram of the electronic circuitry used with the detector ring assembly of FIG. 1.
Figure 5:
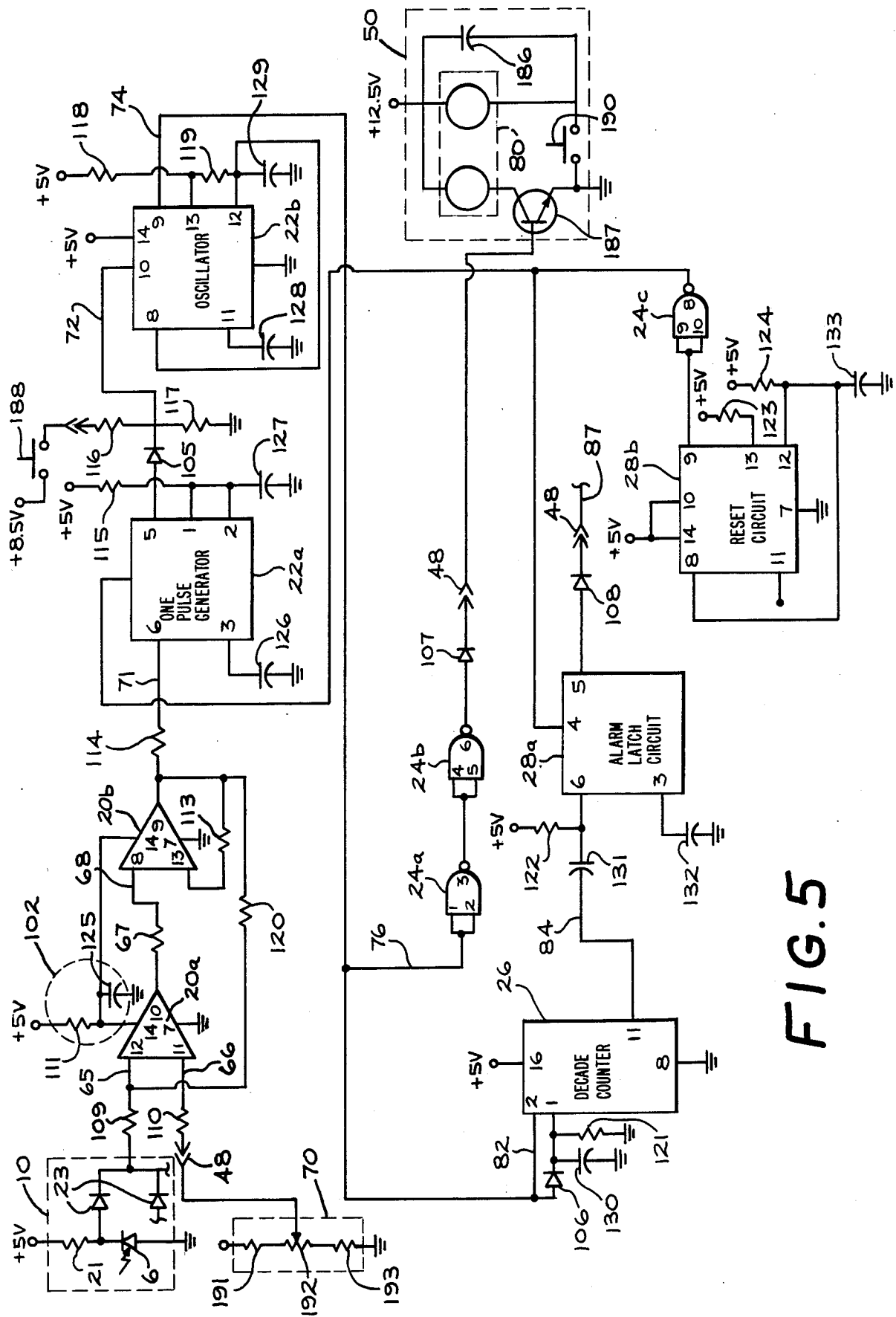
FIG. 5 shows a schematic diagram of an electronic circuit housed in the ring assembly of FIG. 1 as connected to a remotely located electromechanical counter.
Figure 6:
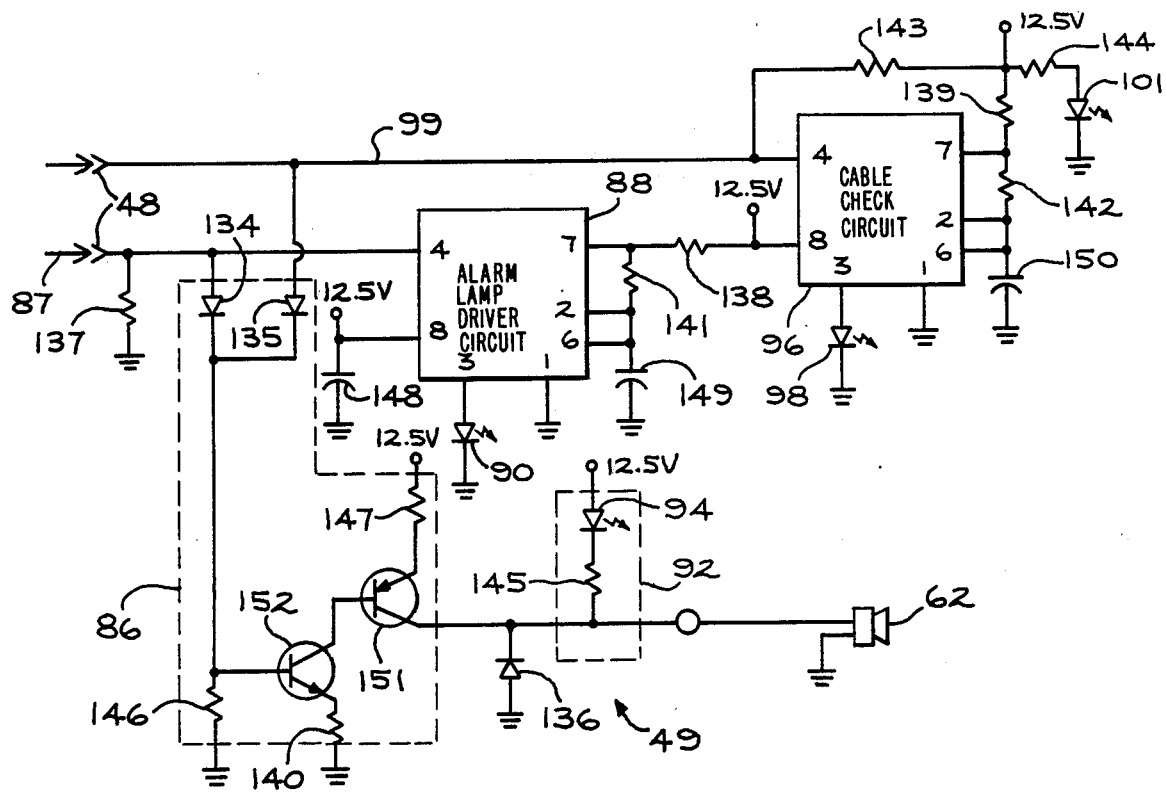
FIG. 6 shows a schematic diagram of an electronic circuit used to detect certain faults which may occur in the electrical system of the subject invention.
Figure 7:
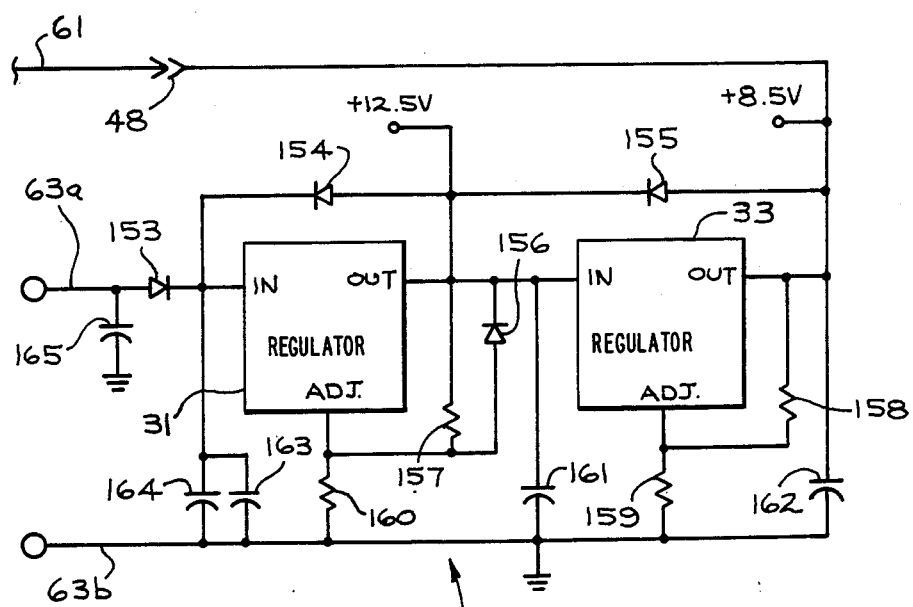
FIG. 7 shows a schematic diagram of regulated 12.5 and 8.5 volt d.c. power supplies for use in the electrical system of the present invention.

IC 28b is connected to IC 22a and IC 28a through line 103 to provide an automatic reset of the one pulse generator 22a and the alarm latch circuit 28a upon application of initial power to the dust detector system through the lines 63a,b (See FIGS. 4–5 and 7). This prevents false tripping of the one pulse generator 22a and insures that the alarm latch circuit 28a is turned off. A power delay circuit 102 is connected to a 5 v. supply terminal of both ICs 20a,b to assure that IC 20a,b will remain energized until after all of the remaining ICs in the circuit of the subject example have become de-energized. This time delay will avoid false triggering of the ICs 20a,b which might otherwise falsely operate the counter 80 and/or the horn 62 when main power is removed from the lines 63a,b.

To complete the description of the circuits of FIGS. 5–8, the following table lists suitable values for all of the components thus shown.

TABLE

| COMPONENT | DESCRIPTION |
|---|---|
| FIG. 5 | |
| *Microcircuits* | |
| IC 20a,b | Motorola LM3900 QUAD OP. AMP. |
| IC 22a,b | Motorola LM556 DUAL TIMER |
| IC 24a,b,c | Motorola SN7437 QUAD NAND GATE |
| IC 26 | Motorola SN74160 DECADE COUNTER |
| IC 28a,b | Motorola NE556 DUAL TIMER |
| *Diodes* | |
| 105, 106 | GE 1N914 |
| 107, 108, | Motorola 1N4002 |
| 6 | Motorola MF0D100 |
| *Resistors* | |
| 192 | 1K Pot. |
| 109, 110, 21 | 10 M, ¼ Watt, 5% |
| 111 | 10 Ohm, ¼ Watt, 5% |
| 69, 113, 124 | 1 M, ¼ Watt, 5% |
| 114 | 3.3K, ¼ Watt, 5% |
| 115 | 2 M, ¼ Watt, 5% |
| 116, 117 | 390 Ohm, ¼ Watt, 5% |
| 118 | 1K, ¼ Watt, 5% |
| 119 | 1.5 M, ¼ Watt, 5% |
| 120 | 22 M, ¼ Watt, 5% |
| 121 | 330, ¼ Watt, 5% |
| 122, 193 | 10K, ¼ Watt, 5% |
| 123 | 4.7K, ¼ Watt, 5% |
| 191 | 15K, ¼ Watt, 5% |
| *Capacitors* | |
| 125 | 1 mfd. |
| 126, 127, 128, 129, 131, 132 | 0.01 mfd. |
| 130 | 50 mfd, 12 v.d.c. |
| 133 | 0.1 mfd. |
| 186 | 25 mfd, 25 v.d.c. |
| *Other Components* | |
| 188, 190 | Hamilin 5806 |
| 187 | RCA 2N6387 |
| 80 | IVO Industries, F329.60A |
| FIG. 6 | |
| *Microcircuits* | |
| IC 88, 96 | Motorola NE555 TIMER |
| *Diodes* | |
| 134, 135, 136 | Motorola 1N4002 |
| *Resistors* | |
| 137, 138, 139, 140 | 1K, ¼ Watt, 5% |
| 141, 142 | 2 M, ¼ Watt, 5% |
| 143 | 1.5K, ¼ Watt, 5% |
| 144, 145 | 36 Ohm, ¼ Watt, 5% |
| 146 | 10K, ¼ Watt, 5% |
| 147 | 3 Ohm, ¼ Watt, 5% |
| *Capacitors* | |
| 148, 149, 150 | 0.1 mfd. |
| *Transistors* | |
| 151 | Motorola MJ11011 |
| 152 | Motorola 2N5682 |
| FIG. 7 | |
| *Microcircuits* | |
| 31, 33 | Motorola LM338K ADJUSTABLE REGULATORS |
| *Diodes* | |
| 153 | Motorola MR750 |
| 154, 155, 156 | Motorola 1N4002 |
| *Resistors* | |
| 157, 158 | 120 Ohm, ¼ Watt, 5% |
| 159 | 680 Ohm, ¼ Watt, 5% |
| 160 | 1.1K, ¼ Watt, 5% |
| *Capacitors* | |
| 161, 162 | 4.7 mfd., 35 volt |
| 163 | 0.01 mfd. |

TABLE-continued

Figure 8:
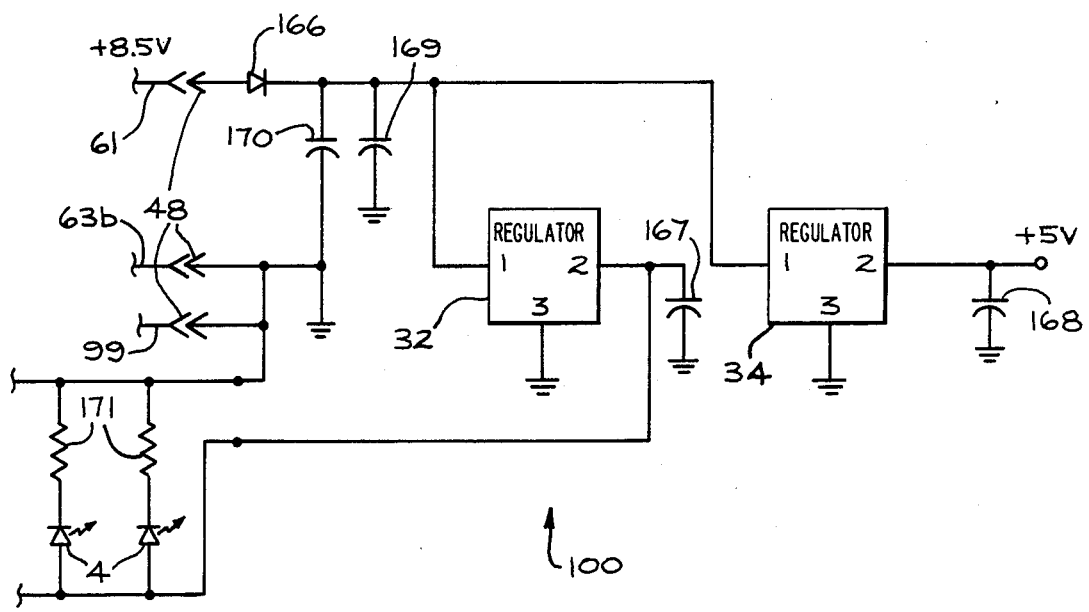
FIG. 8 shows a schematic diagram of a regulated 5.0 volt d.c. power supply for use in the electrical system of the present invention.

| COMPONENT | DESCRIPTION |
|---|---|
| 164 | 3300 mfd., 36 volt |
| 165 | 0.002 mfd, 1 Kv |
| FIG. 8 | |
| Microcircuits | |
| 32, 34 | Motorola LM340TS 5 v. REGULATORS G.E. IN6266 |
| Diodes | |
| 164 | G.E. 1N5626 |
| Resistors | |
| 171 | 91 Ohm, ¼ Watt, 5% |
| Capacitors | |
| 167,168 | 1 mfd. |
| 169 | 0.002 mfd |
| 170 | 2500 mfd., 12 v.d.c. |

Referring now particularly to FIG. 5, there is shown a normally open, magnetically activated reed switch 188 which, when closed, places an 8.5 volt d.c. signal on a reset terminal of the oscillator 22b to selectively produce oscillation thereof to test the alarm circuit. A normally open, magnetically activated reed switch 190 may be closed to reset the counter 80 to zero when desired. The magnetically activated reed switches 188 and 190 may be placed behind a glass window in a display case, not shown, housing the electromegnetic counter 80 and the indicator lights 94, 98 and 101 and can only be activated by placing a small magnet directly in front of each switch, thus making the switches relatively tamper proof. The circuit of the present example is capable of detecting a high speed particle causing only a momentary and partial interruption of one or more of the light beams in the central portion 9. Current variations in the line 65 as small as 30 nanoamperes and light beam interruption times as low as 250 nanoseconds can be detected. The high speed of response of the present circuit is desirable when using the assembly 2 in carburetor air intake systems of turbo charged engines. Other applications of the present invention include particulate matter detection in engine exhaust systems, air filtration systems, air conveying systems, and combustion exhaust systens to name a few. Also it will be apparent that the alarm signal for operating the horn 62 may also, or in the alternative, be used to operate a suitable engine shutdown means such as a conventional solenoid, relay or the like.

It is anticipated that the assembly of the present invention could be adapted readily to provide a rectangular grid of light emitting diodes and light detecting diodes, of the type similar to the diodes 4 and 6 of the presentt example, for use in sensing particle flow in duct systems having rectangular cross-section. Such an arrangement as well as other cross-sectional arrangements are contemplated as being within the scope of the present invention. Of course, other well known types of emitter and detector combinations such as, for example, laser emitter and detector components and conventional photoelectric cells may be arranged in such configurations to produce such a light beam grid. Such components may be substituted for the emitters 4 and detectors 6 of the present example without departing from the spirit of this invention. As previously indicated, the circuits 50, 51, 70, 86, 88, 92, 96 and 144 together with the switches 188, 190, alarm horn 62, and the indicator lamps 90, 94 and 98 are remotely located relative to the circuits contained in the frame 8 on the circuit boards 10 and 18 and are connected to the boards 10 and 18 through conventional multi-wire cable means aand the connector 48, all as indicated in FIG. 4. The cable means thus includes portions of the lines 61, 66, 76, 87, 99 and a portion of the unlabeled line linking the switch 188 to the resistor 116 and line 72.

Although the present invention has been explained with respect to specific details of a certain preferred embodiment thereof, it is not intended that such details limit the scope of this invention otherwise than as specifically set forth in the following claims.

I claim:

1. An apparatus for detecting and counting particulate matter contained in a gaseous medium flowing through a passageway comprising:

a ring assembly forming part of a passageway for the passage of a gaseous medium containing particulate matter therethrough;

a plurality of light beam transmitting means arranged around an interior surface portion of said ring assembly, each of said light beam transmitting means transmitting a light beam across said passageway;

a plurality of means for detecting a light beam mounted around the interior surface portion of said ring assembly, each of said light beam detecting means being diametrically opposite each of said light beam transmitting means for detecting the interruption of the light beam transmitted therefrom when interrupted by particulate matter in the gaseous medium passing through said ring assembly;

means for comparing the total current generated by said light beam detecting means to a reference current and for generating a signal when the total current generated by said light beam detecting means exceeds the reference current;

means for detecting the signal generated by said current comparing means and for generating an output signal in response thereto, the output signal from said signal comparing means being connected back to the input thereof, thereby increasing the response speed of the apparatus;

means for counting the signals generated by said signal detecting means; and means for producing a signal when a predetermined number of signals have been generated by said signal comparing means.

2. The apparatus of claim 1 wherein said light transmitting means and said light detecting means comprise infrared light emitting and detecting diodes, respectively.

3. The apparatus of claim 2 further comprising a ring-shaped infrared filter attached to the interior surface portion of said ring assembly for filtering light transmitted by said light transmitting means and detected by said light detecting means.

4. The apparatus of claim 1 wherein said ring assembly is circular and said light transmitting means and said light detecting means are arranged around the interior surface portion of said ring assembly such that said light beams intersect one another at a common point in said passageway.

5. The apparatus of claim 4 wherein said light detecting means and said light transmitting means are alternately interposed with one another around the interior surface portion of said ring assembly.

6. The apparatus of claim 1 wherein said ring assembly is encased in a suitable epoxy having a series of hollow, cylindrical elements therein.

7. The apparatus of claim 1 wherein said signal means comprises alarm means connected to said counter means for generating an alarm signal when said predetermined number of signals has been counted.

8. The apparatus of claim 7 wherein said alarm means is remotely located relative to said ring assembly and is connected to said counter means by a cable, said apparatus being provided with means for testing the continuity of said cable.

9. The apparatus of claim 1 further comprising means for resetting said counter means when fewer than said predetermined number of signals have been counted within a predetermined time.

10. The apparatus of claim 1 further comprising means for testing said counter means.

11. The apparatus of claim 1 wherein said signal detecting means comprises:
 first oscillator means connected to said current comparing means for generating a continuous high frequency output signal during the period of the current generated by said current comparing means;
 means connected to said first oscillator means for generating a second output signal in the form of a pulse of first time duration upon initiation of said high frequency signal; and
 second oscillator means connected to said current comparing means for producing a third output signal in the form of a pulse having a second time duration which is less than the duration of said pulse of first time duration, said signal detecting means being operable to count the number of pulses of said second time duration generated by said second oscillator.

12. The apparatus of claim 11 wherein said signal detecting means is provided with means for resetting said signal detecting means upon reaching said predetermined number of signals.

13. The apparatus of claim 11 further comprising means connected to said oscillator means for testing said second oscillator means and said signal detecting means and alarm means.

14. The apparatus of claim 11 wherein said signal detecting means is remotely located relative to said ring assembly and is connected to said second oscillator by a cable, said cable being provided with means for testing the continuity thereof.

15. The apparatus of claim 11 further comprising means for maintaining said first oscillator means in a operative condition until after the remainder of said apparatus is de-energized for preventing false triggering of said counter means.

16. An apparatus for detecting and counting the particles entering the air intake of an internal combustion engine comprising:
 a circular ring assembly for connecting with the air intake of an internal combustion engine and having a passageway through which air flows to the engine;
 a plurality of light beam transmitting means arranged in a circle around an interior surface portion of said ring assembly, each of said light beam transmitting means transmitting a light beam across said passageway such that the light beams intersect at a common point in said passageway;
 a plurality of means for detecting a light beam alternately interposed with said light beam transmitting means around the interior surface portion of said ring assembly, each of said light beam detecting means being diametrically opposite each of said light beam transmitting means for detecting the interruption of the light beam transmitted therefrom by the presence of particles in the air flowing through said passageway;
 means for comparing the total current generated by said light beam detecting means to a reference current and for generating a signal when the total current generated by said light beam detecting means exceeds the reference current;
 means for detecting the signal generated by said current comparing means and for generating an output signal in response thereto, the output signal from said signal comparing means being connected back to an input thereof, thereby increasing the response speed of the apparatus;
 means for counting the signals produced by said current comparing means; and
 means for producing an output signal when a predetermined number of signals have been produced by said comparing means.

17. A method for detecting and counting the particles contained in a gaseous medium flowing through a passageway comprising:
 drawing a gaseous medium containing particulate matter therein through a passageway having a detection apparatus therein;
 transmitting a plurality of light beams from a plurality of individual light beam transmitting means arranged around an interior surface of the passageway through which the gaseous medium is drawn through the gaseous medium being drawn through said detection apparatus;
 detecting each of the light beams transmitted through the gaseous medium with a plurality of light beam detecting means, each of the light beam detecting means detecting the light beam transmitted by one of the light beam transmitting means and generating a current in response to the light beam detected;
 comparing the change in the total current produced by the light detecting means in response to the interruption of the light beams transmitted by the light beam transmitting means by particulate matter contained in said flow of gaseous medium to a current level, said current level corresponding to a preselected amount of interruption by said particles;
 generating a signal when the current produced by the light detecting means exceeds said current level;
 counting the number of signals generated as a result of said comparison; and
 producing a signal when the number of counted signals reaches a predetermined number within a predetermined time.

18. The method of claim 19 further comprising generating a high frequency output signal during the duration of the signal generated in response to the interruption of any one of said light beams, sending the high frequency output signal so generated to a circuit means for generating a signal in the form of a pulse having a first time duration, and producing a signal in the form of a pulse having a second time duration which is less than said first time duration in response to said pulse having a first time duration, and counting the number of pulses of said second time duration.

19. The method of claim 18 further comprising producing a signal when the number of pulses of said second time duration reaches a predetermined number within a predetermined time.

20. The method of claim 17 further comprising feeding the signal generated when the current produced by the light detecting means exceeds said current level back into the current generated by the light detecting means.

* * * * *